United States Patent [19]

Wang et al.

[11] Patent Number: 5,521,299

[45] Date of Patent: May 28, 1996

[54] OLIGONUCLEOTIDES FOR DETECTION OF BACULOVIRUS INFECTION

[75] Inventors: Chung-Hsiung Wang; Chu-Fang Lo; Guang-Hsung Kou; Chang-Jen Huang; Chih-Ming Chou, all of Taipei, Taiwan

[73] Assignee: National Science Council, Taiwan

[21] Appl. No.: 343,379

[22] Filed: Nov. 22, 1994

[51] Int. Cl.$^6$ ............ C07H 21/04; C12P 19/34; C12Q 1/68
[52] U.S. Cl. ............ 536/24.3; 536/24.32; 435/6; 435/91.2
[58] Field of Search ............ 435/91.2, 6; 536/24.3

[56] References Cited

U.S. PATENT DOCUMENTS 4,683,202  7/1987  Mullis ............ 435/91

OTHER PUBLICATIONS

Chang et al., "Purification and Amplification of DNA from *Penaeus monodon*–Type Baculovirus (MBV)," Journal of Invertebrate Pathology 62:116–120, 1993.
Gonzalez et al., "Insertion of the SfMNPV Polyhedrin Gene into an AcMNPV Polyhedrin Deletion Mutant during during Viral Infection," Virology 170:160–175, 1989.
Iatrou et al., "Polyhedrin Gene of *Bombyx mori* Nuclear Polyhedrosis Virus,", Journal of Virology 54:436–445, 1985.
Hooft Van Iddekinge et al., "Nucleotide Sequence of the Polyhedrin Gene of *Autographa californica* Nuclear Polyhedrosis Virus," Virology 131:561–565, 1983.
Kuzio et al., "Nucleotide Sequence of the p10 Polypeptide Gene of *Autographa californica* Nuclear Polyhedrosis Virus," Virology 139:414–418, 1984.
Leisy et al., "Nucleotide Sequencing and Transcriptional Mapping of the *Orgyia pseudotsugata* Multicapsid Nuclear Polyhedrosis Virus p10 Gene," Virology 153:157–167, 1986.
Leisy et al., "Location and Nucleotide Sequence of the *Orgyia pseudotsugata* Single Nucleocapsid Nuclear Polyhedrosis Virus Polyhedrin Gene," The Journal of General Virology, 67:1073–1079, 1986.
Leisy et al., "The Nucleotide Sequence of the Polyhedrin Gene Region from the Multicapsid Baculovirus of *Orgyia pseudotsugata*," Virology vol. 153:280–288, 1986.
Malitschek et al., "Rapid Identification of Recombinant Baculoviruses Using PCR," BioTechniques, 11:177–178, 1991.

*Primary Examiner*—W. Gary Jones
*Assistant Examiner*—Jeffrey Fredman
*Attorney, Agent, or Firm*—Fish & Richardson

[57]  ABSTRACT

Two pairs of PCR primer mixtures to be used to detect baculovirus infection: (i) a mixture of 25 to 35-base oligonucleotides including, respectively, 5'-TTTTGACGCAAATYYTAGACGCCGT-3' (SEQ ID NO: 1), and a mixture of 19 to 29-base oligonucleotides, including, respectively, 5'-TCARYATKGATTGAATWTC-3' (SEQ ID NO: 2); and (ii) a mixture of 30 to 40-base oligonucleotides, including, respectively, 5'-TAYGTGTACGACAACAARTAY-3' (SEQ ID NO: 3), and a mixture of 30 to 40-base oligonucleotides, including, respectively, 5'-GCGTCKGGYGCAAAYTCYTTWACY-3' (SEQ ID NO: 7).

16 Claims, 1 Drawing Sheet

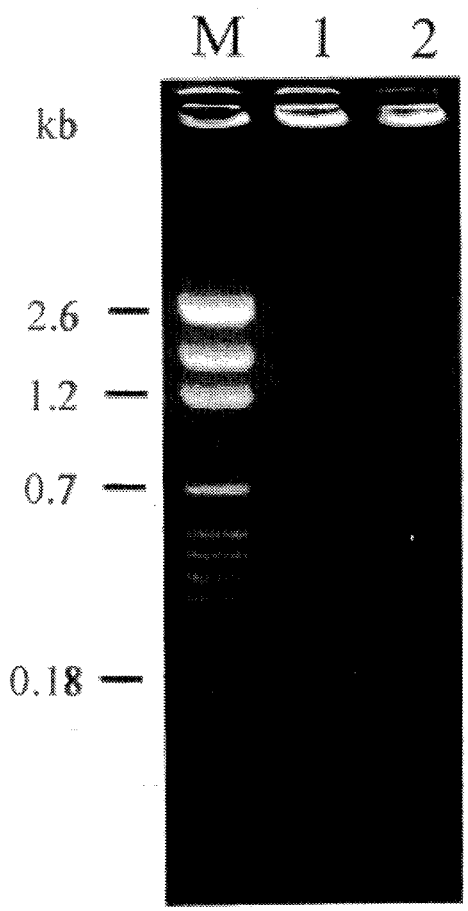 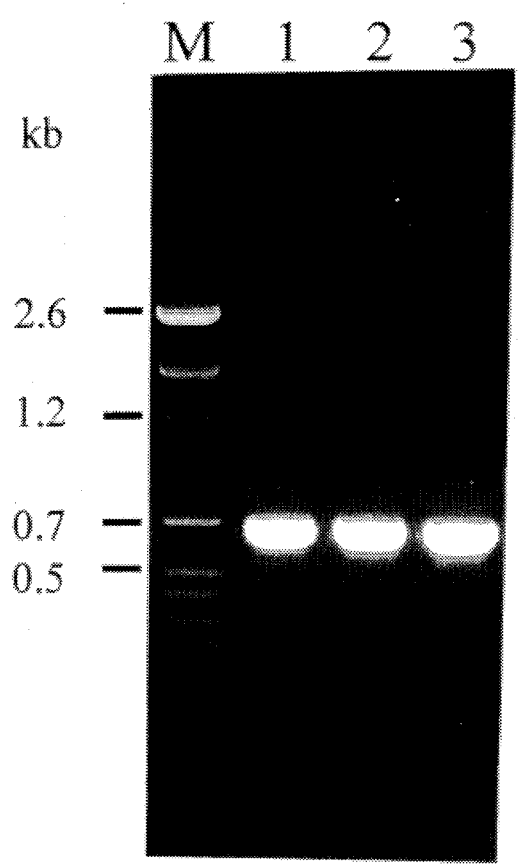
FIG. 1
FIG. 2

OLIGONUCLEOTIDES FOR DETECTION OF BACULOVIRUS INFECTION

BACKGROUND OF THE INVENTION

Polyhedrosis of arthropods infected with baculoviruses, such as the nuclear polyhedrosis virus ("NPV"), has jeopardized the shellfish culturing industry in Taiwan. Thus, there is a need to develop a method for rapid detection of baculovirus infection.

The widely used polymerase chain reaction ("PCR") technique, which enables one to amplify a specific DNA segment to a detectable amount in a matter of hours, may be used to determine the presence or absence of a specific DNA sequence if a pair of highly selective PCR primers are available. See U.S. Pat. Nos. 4,683,195 and 4,683,202, both of which are hereby incorporated by reference.

SUMMARY OF THE INVENTION

The present invention relates to PCR primers which can be used to detect infection of arthropods with baculoviruses.

An aspect of this invention relates to a pair of PCR primer mixtures: (i) a first set (i.e., mixture) of PCR primers or single-stranded oligonucleotides, each of which contains 25–35 bases, for a first priming sequence, the primers in this set including, respectively, the following DNA segments: 5'- TTTTGACGCAAATYYTAGACGCCGT -3' (SEQ ID NO: 1) [e.g., 5'- TTTTGACGCAAATYYTAGACGCCGT -3' (SEQ ID NO: 1)]; and (ii) a second set of PCR primers each containing 19–29 nucleotides, for a second priming sequence, the primers of this set including, respectively, the following DNA segments: 5'- TCARYATKGATTGAATWTC -3' (SEQ ID NO: 2) [e.g., 5'- TCARYATKGATTGAATWTC -3' (SEQ ID NO: 2)].

A further aspect of this invention relates to another pair of PCR primer mixtures: (i) a third set of PCR primers each containing 30–40 nucleotides for a third priming sequence, the primers of the third set including, respectively, the following DNA segments: 5'- TAYGTGTAC GACAACAARTAY -3' (SEQ ID NO: 3) [e.g., 5'- TAYGTGTACGA CAACAARTAY -3' (SEQ ID NO: 3), 5'- ACYTAYGTGTACGACAACAAR TAY -3' (SEQ ID NO: 4), 5'- TAYGTGTACGACAACAARTAYTACAAA -3' (SEQ ID NO: 5), or 5'- ACYTAYGTGTACGACAACAARTAYTACAAA -3' (SEQ ID NO: 6)]; and (ii) a fourth set of PCR primers each containing 30–40 nucleotides for a fourth priming sequence, the primers of this set including, respectively, the following DNA segments: 5'- GCGTCKGGYGCAAAYTCYTTWACY -3' (SEQ ID NO: 7) [e.g., 5'- GCGTCKGGYGCAAAYTCYTTWACY -3' (SEQ ID NO: 7), 5'- GGYGCGTCKGGYGCAAAYTCYTTWACY -3' (SEQ ID NO: 8), 5'- GCGTCKGGYGCAAAYTCYTTWACYTTRAA -3' (SEQ ID NO: 9), or 5'- GGYGCGTCKGGYGCAAAYTCYTTWACYTTRAA -3' (SEQ ID NO: 10)].

The base codes used herein are as follows: Y stands for C or T, W stands for A or T, K stands for G or T, and R stands for A or G.

Thus, a set of oligonucleotides of this invention is a mixture of oligonucleotides, which, with high sequence similarity, bind to the same priming sequence in the candidate DNA targets. As an example, the first set of oligonucleotides, i.e., 5'- TTTTGACGCAAATYYTAGACGCCGT -3' (SEQ ID NO: 1), is a mixture containing the following four oligonucleotides (preferably in equimolar amounts):

5'- TTTTGACGCAAATCCTAGACGCCGT -3' (SEQ ID NO: 11),

5'- TTTTGACGCAAATCTTAGACGCCGT -3' (SEQ ID NO: 12),

5'- TTTTGACGCAAATTCTAGACGCCGT -3' (SEQ ID NO: 13), and

5'- TTTTGACGCAAATTTTAGACGCCGT -3' (SEQ ID NO: 14).

During PCR amplification, an oligonucleotide from the first set and an oligonucleotide from the second set constitute a primer pair and bind to the first and second priming sequences, respectively, in a DNA target, if any, respectively, before the DNA segment encompassed by the two priming sequences is amplified. The same is true for an oligonucleotide from the third set and an oligonucleotide from the fourth set, as the third and fourth sets are a pair of PCR primer mixtures.

Other features and advantages of the present invention will be apparent from the following drawings and description of the preferred embodiments, and also from the appending claims.

BRIEF DESCRIPTION OF THE DRAWINGS

The drawings are first described.

FIG. 1 is a photograph of agarose gel electrophoresis which shows the detection of infection of insects with *Autographa californica* nuclear polyhedrosis virus ("AcNPV") and *Perina nuda* nuclear polyhedrosis virus ("PnNPV") by PCR amplification using a pair of primer mixtures of this invention.

FIG. 2 is a photograph of agarose gel electrophoresis which shows the detection of infection of insects with *Autographa californica* nuclear polyhedrosis virus ("AcNPV"), *Perina nuda* nuclear polyhedrosis virus ("PnNPV"), and *Bombyx mori* nuclear polyhedrosis virus ("BmNPV") by PCR amplification using another pair of primer mixtures of this invention.

DESCRIPTION OF THE PREFERRED EMBODIMENTS

The hitherto reported NPV strains include, but are not limited to, *Perina nuda* nuclear polyhedrosis virus ("PnNPV"), *Orgyia pseudotsugata* nuclear polyhedrosis virus ("OpNPV"), *Autographa californica* nuclear polyhedrosis virus ("AcNPV"), *Mamestra brassicae* nuclear polyhedrosis virus ("MbNPV"), *Spodoptera frugiperda* nuclear polyhedrosis virus ("SfNPV"), and *Bombyx mori* nuclear polyhedrosis virus ("BmNPV"). We have developed a system to detect the infection with various NPV's.

More specifically, the present invention provides two pairs of primer mixtures (see Summary of the Invention, supra) for PCR amplification of two DNA fragments of known lengths located within the polyhedrin gene and the p10 gene, respectively. The sequences of the AcMNPV polyhedrin gene, AcMNPV p10 gene, OpMNPV polyhedrin gene, OpMNPV p10 gene, BmSNPV polyhedrin gene, OpMNPV polyhedrin gene, and SfMNPV polyhedrin gene can be found in Hooft van Iddekinge et al., Virology 131:561 (1983); Kuzio et al., Virology 139:414 (1984); Leisy et al., Virology 153:280 (1986); Leisy et al., Virology 153:157 (1986); Iatrou et al., J. Virol. 54:436 (1985); Leisy et al., J. Gen. Virol. 67:1073 (1986); and Gonzalez et al., Virology 170:160 (1989), all of which are hereby incorporated by reference.

Either pair of primer mixtures of this invention can be used to diagnose the infection of an arthropod with a NPV. More specifically, DNA fragments are first extracted from the host cells, such as the blood cells for insects and the hepatopancreatic gland for shellfish. PCR is then performed to amplify a target DNA fragment (i.e., encompassed by the PCR primers), if any. The detection of an amplification product with a size corresponding to that of the target DNA fragment by agarose gel electrophoresis or otherwise strongly suggests infection.

A labeled nucleotide (such as a radio-labeled nucleotide, e.g., $^{32}$P-dATP; a fluorochrome-labeled nucleotide, e.g., digoxigenin-11-dATP; or an enzyme-labeled nucleotide, e.g., alkaline phosphatase-dATP) can also be used in the just-described PCR process for the production of a labeled amplification product to be used as a probe to determine, by a hybridization assay, the presence of a target viral DNA in an arthropod suspected of being infected with a NPV.

One skilled in the art can, based on the description herein, utilize the present invention to its fullest extent. The following specific embodiments are, therefore, to be construed as merely illustrative, and not limitative of the remainder of the disclosure in any way whatsoever. Without further elaboration, it is noted that the techniques required to practice the claimed invention are within the ability of a person of ordinary skill in the art, and in any event can be readily found in the literature, e.g., see Sambrook, et al. Molecular Cloning, A Laboratory Manual, 2nd Ed. Cold Spring Harbor Laboratory Press, New York (1989); and Current Protocols in Molecular Biology, Ed. Ausubel et al., John Wiley & Sons, New York (1989), both of which are hereby incorporated by reference in their entirety. Note that primers used in the following examples were synthesized by Biosynthesis Inc., Lewisville, Tex.

EXAMPLE 1: Detection of Infection with AcNPV by PCR amplification of a p10 gene fragment The PCR amplification method used herein to detect the infection with a NPV is disclosed in Malitschek et al., BioTechniques, 11:177 (1991), which is hereby incorporated by reference. An insect, *Autographa californica,* which was suspected of being infected by AcNPV was added into 0.5 ml of TE buffer (10 mM Tris-HCl, 1 mM EDTA, pH=7.5) and was homogenized in ice. The homogenized insect was centrifuged at 13,000 rpm for 10 minutes to give a supernatant. After 10 µl of the supernatant was added to 90 µl of detergent buffer A (50 mM KCl, 10 mM Tris-HCl, pH=8.3, 0.1 mg/ml gelatin, 0.45% NP-40, 0.45% Tween-20), followed by addition of proteinase K (10 µg) and reaction at 60° C. for 1 hour. The reaction mixture was then heated to boiling for 10 minutes. 50 µl of the reaction mixture was used as a template for PCR amplification. Four nucleotides (dGTP, dATP, dTTP, dCTP, each final concentration 0.25 mM) were added with a pair of primer mixtures, i.e., SEQ ID NO: 1 and SEQ ID NO: 2 (0.5 µg each), Taq DNA polymerase (2.5 U purchased from Promega company) and detergent buffer B 250 mM $MgCl_2$, 10X detergent buffer A) to a total volume of 100 µl. The mixture was then placed into a PCR apparatus, 1 cycle of the reaction being set as follows: 94° C. for denaturing (1 minutes), 42° C. for annealing (1 minute) and 72° C. for elongation (5 minutes). After 40 cycles, a PCR product (in 10 µl reaction mixture), with the expected size of 160 bp, was ascertained on an ethidium bromide-stained agarose electrophoresis gel. See lane 1 of FIG. 1 (M denotes molecular markers; Promega PGEM markers).

EXAMPLE 2: Detection of Infection with PnNPV by PCR amplification of a p10 gene fragment The same process as that described in Example 1 was performed except that an insect, *Perina nuda,* which was suspected of being infected by PnNPV, was used. Again, a PCR product of the expected size (160 bp) was observed. See lane 2 of FIG. 1.

EXAMPLE 3: Detection of Infection with AcNPV by PCR amplification of a polyhedrin gene fragment The same process as that described in Example 1 was performed except that another pair of primer mixtures, SEQ ID NO: 6 and SEQ ID NO: 10, were used. A PCR amplification product of the expected size (680 bp) was observed. See lane 1 of FIG. 2 (M denotes molecular markers; Promega PGEM markers).

EXAMPLE 4: Detection of Infection with BmNPV by PCR amplification of a polyhedrin gene fragment The same process as that described in Example 3 was performed except that an insect, *Bombyx mori,* which was suspected of being infected by BmNPV, was used. Again, a PCR product of the expected size (680 bp) was observed. See lane 2 of FIG. 2.

EXAMPLE 5: Detection of Infection with PnNPV by PCR amplification of a polyhedrin gene fragment The same process as that described in Example 3 was performed except that an insect, *Perina nuda,* which was suspected of being infected by PnNPV, was used. Again, a PCR product of the expected size (680 bp) was observed. See lane 3 of FIG. 2.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A set of single-stranded oligonucleotides, said set of oligonucleotides consisting of the following DNA sequences:

5'- TTTTGACGCAAATYYTAGACGCCGT -3' (SEQ ID NO: 1), wherein Y is C or T.

2. A set of single-stranded oligonucleotides, said set of single-stranded oligonucleotides consisting of the following DNA sequences:

5'- TCARYATKGATTGAATWTC -3' (SEQ ID NO: 2), wherein W is A or T, K is G or T, Y is C or T, and R is A or G.

3. A set of single-stranded oligonucleotides of claim 1 and an additional set of single-stranded oligonucleotides, said additional set of single-stranded oligonucleotides consisting of the following DNA sequences:

5'- TCARYATKGATTGAATWTC -3' (SEQ ID NO: 2), wherein W is A or T, K is G or T, and R is A or G.

4. A set of single-stranded oligonucleotides, said set of single-stranded oligonucleotides consisting of the following DNA sequences:

5'- TAYGTGTACGACAACAARTAY -3 ' (SEQ ID NO: 3), wherein Y is C or T, and R is A or G.

5. A set of single-stranded oligonucleotides of claim 4, said single-stranded oligonucleotides consisting of

5'- TAYGTGTACGACAACAARTAY -3' (SEQ ID NO: 3),

5'- ACYTAYGTGTACGACAACAARTAY -3' (SEQ ID NO: 4),

5'- TAYGTGTACGACAACAARTAYTACAAA -3' (SEQ ID NO: 5), or

5'- ACYTAYGTGTACGACAACAARTAYTACAAA -3' (SEQ ID NO: 6).

6. A set of single-stranded oligonucleotides of claim 5, said set of single-stranded oligonucleotides consisting of 5'- ACYTAYGTGTACGACAACAARTAYTACAAA -3' (SEQ ID NO: 6).

7. A set of single-stranded oligonucleotides, said set of single-stranded oligonucleotides consisting of the following DNA sequences:

5'- GCGTCKGGYGCAAAYTCYTTWACY -3' (SEQ ID NO: 7), wherein Y is C or T, W is A or T, and K is G or T.

8. A set of single-stranded oligonucleotides of claim 7, said set of single-stranded oligonucleotides consisting of

5'- GCGTCKGGYGCAAAYTCYTTWACY -3' (SEQ ID NO: 7),

5'- GGYGCGTCKGGYGCAAAYTCYTTWACY -3' (SEQ ID NO: 8),

5'- GCGTCKGGYGCAAAYTCYTTWACYTTRAA -3' (SEQ ID NO: 9), or

5'- GGYGCGTCKGGYGCAAAYTCYTTWACYTTRAA -3' (SEQ ID NO: 10), wherein R is A or G.

9. A set of single-stranded oligonucleotides of claim 8, said single-stranded oligonucleotides consisting of 5'-GGYGCGTCKGGYGCAAAYTCYTTWACYTTRAA -3' (SEQ ID NO: 10).

10. A set of single-stranded oligonucleotides of claim 4, and an additional set of single-stranded oligonucleotides, said additional set of single-stranded oligonucleotides consisting of the following DNA sequences:

5'- GCGTCKGGYGCAAAYTCYTTWACY -3' (SEQ ID NO: 7), wherein W is A or T, and K is G or T.

11. A set of single-stranded oligonucleotides of claim 10, wherein said additional set of single-stranded oligonucleotides consisting of

5'- GCGTCKGGYGCAAAYTCYTTWACY -3' (SEQ ID NO: 7),

5'- GGYGCGTCKGGYGCAAAYTCYTTWACY -3' (SEQ ID NO: 8),

5'- GCGTCKGGYGCAAAYTCYTTWACYTTRAA -3' (SEQ ID NO: 9), or

5'- GGYGCGTCKGGYGCAAAYTCYTTWACYTTRAA -3' (SEQ ID NO: 10).

12. A set of single-stranded oligonucleotides of claim 5, and an additional set of single-stranded oligonucleotides, said additional set of single-stranded oligonucleotides consisting of the following DNA sequences:

5'- GCGTCKGGYGCAAAYTCYTTWACY -3' (SEQ ID NO: 7), wherein W is A or T, and K is G or T.

13. A set of single-stranded oligonucleotides of claim 5, and an additional set of single-stranded oligonucleotides, said additional set of single-stranded oligonucleotides consisting of

5'- GCGTCKGGYGCAAAYTCYTTWACY -3' (SEQ ID NO: 7),

5'- GGYGCGTCKGGYGCAAAYTCYTTWACY -3' (SEQ ID NO: 8),

5'- GCGTCKGGYGCAAAYTCYTTWACYTTRAA -3' (SEQ ID NO: 9), or

5'- GGYGCGTCKGGYGCAAAYTCYTTWACYTTRAA -3' (SEQ ID NO: 10), wherein W is A or T, and K is G or T.

14. A set of single-stranded oligonucleotides of claim 13, wherein said additional set of single-stranded oligonucleotides are 5'- GGYGCGTCKGGYGCAAAYTCYTTWACYTTRAA -3' (SEQ ID NO: 10).

15. A set of single-stranded oligonucleotides of claim 6, further comprising an additional set of single-stranded oligonucleotides, said additional single-stranded oligonucleotides consisting of

5'- GCGTCKGGYGCAAAYTCYTTWACY -3' (SEQ ID NO: 7),

5'- GGYGCGTCKGGYGCAAAYTCYTTWACY -3' (SEQ ID NO: 8),

5'- GCGTCKGGYGCAAAYTCYTTWACYTTRAA -3' (SEQ ID NO: 9), or

5'- GGYGCGTCKGGYGCAAAYTCYTTWACYTTRAA -3' (SEQ ID NO: 10), wherein W is A or T, and K is G or T.

16. A set of single-stranded oligonucleotides of claim 15, wherein said additional set of single-stranded oligonucleotides consisting of 5'- GGYGCGTCKGGYGCAAAYTCYTTWACYTTRAA -3' (SEQ ID NO: 10).

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i x ) FEATURE:
        ( D ) OTHER INFORMATION: Y equals C or T ( x i ) SEQUENCE DESCRIPTION: SEQ ID NO: 1:

TTTTGACGCA AATYYTAGAC GCCGT        25

( 2 ) INFORMATION FOR SEQ ID NO: 2:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i x ) FEATURE:
        ( D ) OTHER INFORMATION: K equals G or T
            R equals A or G
            W equals A or T
            Y equals C or T ( x i ) SEQUENCE DESCRIPTION: SEQ ID NO: 2:

TCARYATKGA TTGAATWTC        19

( 2 ) INFORMATION FOR SEQ ID NO: 3:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i x ) FEATURE:
        ( D ) OTHER INFORMATION: R equals A or G
            Y equals C or T ( x i ) SEQUENCE DESCRIPTION: SEQ ID NO: 3:

TAYGTGTACG ACAACAARTA Y        21

( 2 ) INFORMATION FOR SEQ ID NO: 4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i x ) FEATURE:
        ( D ) OTHER INFORMATION: R equals A or G
            Y equals C or T ( x i ) SEQUENCE DESCRIPTION: SEQ ID NO: 4:

ACYTAYGTGT ACGACAACAA RTAY        24

( 2 ) INFORMATION FOR SEQ ID NO: 5:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i x ) FEATURE:
        ( D ) OTHER INFORMATION: R equals A or G
            Y equals C or T (xi) SEQUENCE DESCRIPTION: SEQ ID NO: 5:

TAYGTGTACG ACAACAARTA YTACAAA                                  27

(2) INFORMATION FOR SEQ ID NO: 6:

(i) SEQUENCE CHARACTERISTICS:
      (A) LENGTH: 30
      (B) TYPE: nucleic acid
      (C) STRANDEDNESS: single
      (D) TOPOLOGY: linear (ix) FEATURE:
      (D) OTHER INFORMATION: R equals A or G
          Y equals C or T (xi) SEQUENCE DESCRIPTION: SEQ ID NO: 6:

ACYTAYGTGT ACGACAACAA RTAYTACAAA                               30

(2) INFORMATION FOR SEQ ID NO: 7:

(i) SEQUENCE CHARACTERISTICS:
      (A) LENGTH: 24
      (B) TYPE: nucleic acid
      (C) STRANDEDNESS: single
      (D) TOPOLOGY: linear (ix) FEATURE:
      (D) OTHER INFORMATION: K equals G or T
          W equals A or T
          Y equals C or T (xi) SEQUENCE DESCRIPTION: SEQ ID NO: 7:

GCGTCKGGYG CAAAYTCYTT WACY                                     24

(2) INFORMATION FOR SEQ ID NO: 8:

(i) SEQUENCE CHARACTERISTICS:
      (A) LENGTH: 27
      (B) TYPE: nucleic acid
      (C) STRANDEDNESS: single
      (D) TOPOLOGY: linear (ix) FEATURE:
      (D) OTHER INFORMATION: K equals G or T
          W equals A or T
          Y equals C or T (xi) SEQUENCE DESCRIPTION: SEQ ID NO: 8:

GGYGCGTCKG GYGCAAAYTC YTTWACY                                  27

(2) INFORMATION FOR SEQ ID NO: 9:

(i) SEQUENCE CHARACTERISTICS:
      (A) LENGTH: 29
      (B) TYPE: nucleic acid
      (C) STRANDEDNESS: single
      (D) TOPOLOGY: linear (ix) FEATURE:
      (D) OTHER INFORMATION: K equals G or T
          R equals A or G
          W equals A or T
          Y equals C or T (xi) SEQUENCE DESCRIPTION: SEQ ID NO: 9:

GCGTCKGGYG CAAAYTCYTT WACYTTRAA                                29

(2) INFORMATION FOR SEQ ID NO: 10:

( i ) SEQUENCE CHARACTERISTICS:
    ( A ) LENGTH: 32
    ( B ) TYPE: nucleic acid
    ( C ) STRANDEDNESS: single
    ( D ) TOPOLOGY: linear ( i x ) FEATURE:
    ( D ) OTHER INFORMATION: K equals G or T
        R equals A or G
        W equals A or T
        Y equals C or T ( x i ) SEQUENCE DESCRIPTION: SEQ ID NO: 10:

GGYGCGTCKG GYGCAAAYTC YTTWACYTTR AA    32

( 2 ) INFORMATION FOR SEQ ID NO: 11:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 11:

TTTTGACGCA AATCCTAGAC GCCGT    25

( 2 ) INFORMATION FOR SEQ ID NO: 12:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 12:

TTTTGACGCA AATCTTAGAC GCCGT    25

( 2 ) INFORMATION FOR SEQ ID NO: 13:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 13:

TTTTGACGCA AATTCTAGAC GCCGT    25

( 2 ) INFORMATION FOR SEQ ID NO: 14:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 14:

TTTTGACGCA AATTTTAGAC GCCGT    25